US008403906B2

(12) United States Patent
Buck et al.

(10) Patent No.: US 8,403,906 B2
(45) Date of Patent: Mar. 26, 2013

(54) INTEGRATED PHARMACEUTICAL PRODUCTION, QUALITY, ASSURANCE, AND SAFETY SYSTEM (IQS)

(75) Inventors: Oliver Buck, Bayerisch Gmain (DE); Christoph Ehlers, Freiburg (DE); Tuomo Nikula, Stutensee (DE); Michael Schilp, Garching (DE)

(73) Assignee: Isotopen Technologien Munchen AG, Bad Reichenhall (DE)

( * ) Notice: Subject to any disclaimer, the term of this patent is extended or adjusted under 35 U.S.C. 154(b) by 1299 days.

(21) Appl. No.: 11/793,467

(22) PCT Filed: Apr. 4, 2006

(86) PCT No.: PCT/EP2006/003062

§ 371 (c)(1),
(2), (4) Date: Sep. 21, 2007

(87) PCT Pub. No.: WO2006/105936

PCT Pub. Date: Oct. 12, 2006

(65) Prior Publication Data

US 2008/0140046 A1 Jun. 12, 2008

(30) Foreign Application Priority Data

Apr. 6, 2005 (DE) ........................ 10 2005 015 843

(51) Int. Cl.
*A61B 19/00* (2006.01)

(52) U.S. Cl. ........................................................ 604/407

(58) Field of Classification Search .......... 604/403–416; 424/1.11; 422/501–504, 509–515; 73/863.32
See application file for complete search history.

(56) References Cited

U.S. PATENT DOCUMENTS 5,415,843 A * 5/1995 Andersson .................... 422/159
2002/0035412 A1 3/2002 Kircher et al.
2004/0028573 A1 2/2004 Schmitz et al.

FOREIGN PATENT DOCUMENTS

DE 19824057 C1 7/1999
DE 19817328 C2 8/2000
WO WO 99/63547 A2 12/1999

* cited by examiner

*Primary Examiner* — Philip R Wiest
(74) *Attorney, Agent, or Firm* — Saliwanchik, Lloyd & Eisenschenk

(57) ABSTRACT

A therapy module for providing a diagnostic or therapeutic substance combination, including at least two containers adapted to be interconnected for taking up at least one substance, and means or part of a means for supplying a quantity of the at least one substance from one of the containers into another container of the therapy module.

21 Claims, 1 Drawing Sheet

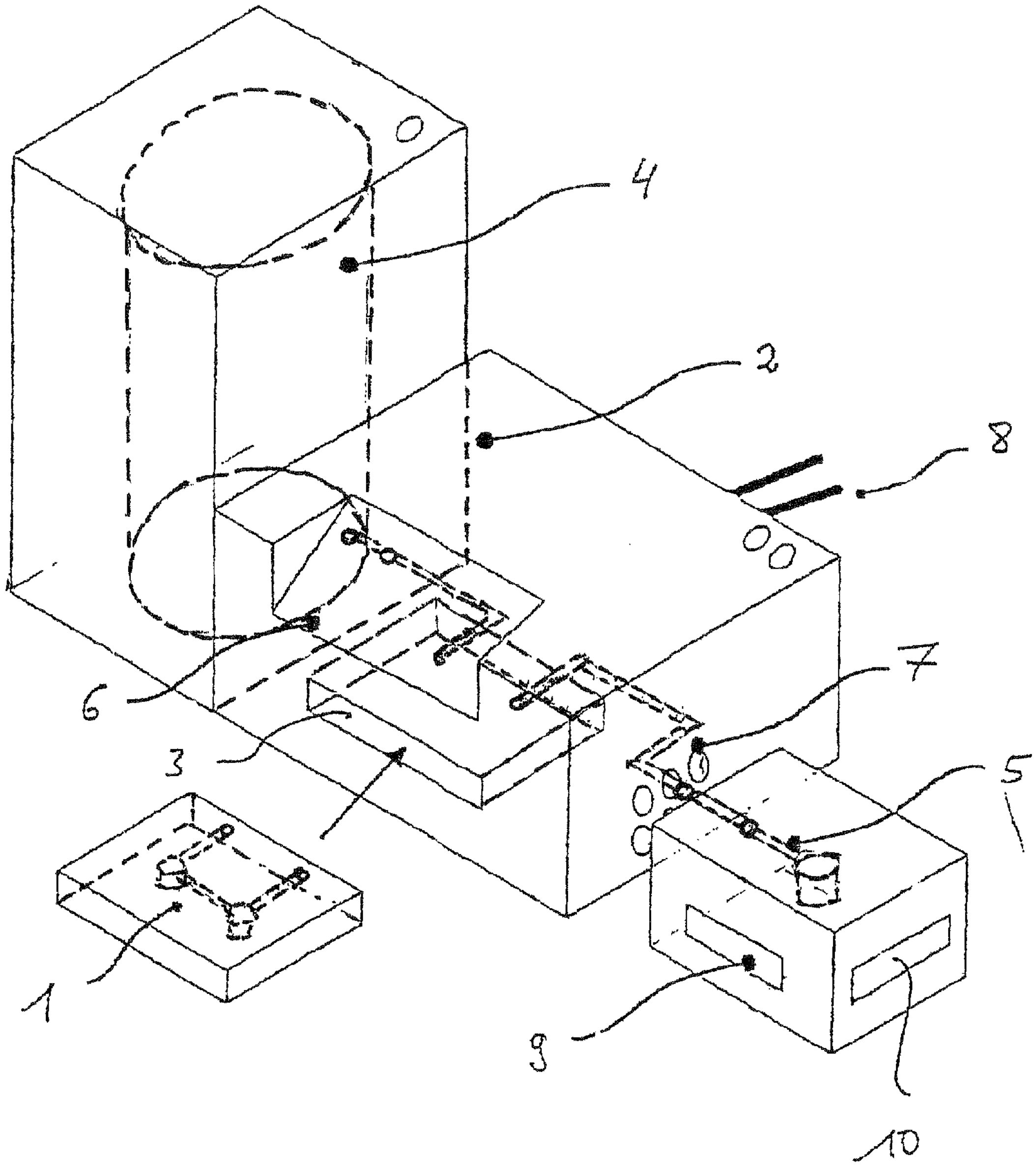
4
2
8
6
7
3
5
1
9
10

INTEGRATED PHARMACEUTICAL PRODUCTION, QUALITY, ASSURANCE, AND SAFETY SYSTEM (IQS)

CROSS-REFERENCE TO RELATED APPLICATION

This application is the U.S. National Stage Application of International Patent Application No. PCT/EP2006/003062, filed Apr. 4, 2006, the disclosure of which is hereby incorporated by reference herein in its entirety, including any figures, tables, or drawings.

The instant invention relates to a system and components for providing a diagnostic or therapeutic substance combination, especially for providing a diagnostic or therapeutic combination of substances including a short-lived substance, and also relates to a corresponding method.

Diagnostic or therapeutic substance combinations containing short-lived substances, such as short-lived chemical agents, live cells, proteins, or radioactive substances are used in certain treatments, i.e. therapeutic and diagnostic applications.

An essentially quite generally valid scheme of process steps can be laid down for many treatments including the use of short-lived substances, beginning with a patient's diagnosis to administration of medicines and final diagnostics.

Following diagnosis and the decision to take up a certain therapy and its corresponding planning, the process steps typically include the preparation of a medicine by combining a plurality of substances needed for treatment and developed for that purpose, furthermore, quality control of the medicine thus prepared, and converting the medicine into a form for administration, and finally administering the medicine.

Within the framework of treatment, based on a patient's diagnosis, data are generated regarding, for example, the patient's constitution, general symptoms of the disease, the development of the genetic expression of certain targets, and thus the suitability of certain purposive forms of treatment, the kind of therapy and its strategy, frequency and intervals of treatment, as well as the individual doses of medicines or diagnostic substances to be administered each time, and also the necessay control, checking, and extended care. Up to now these data, as a rule, are collected "manually" and recorded in patient files which may be memorized in a computer.

The next step is the preparation of the starting materials or substances for the medicine which may include chemically and/or biologically short-lived or radioactive substances but may also comprise other biological or chemical agents which are substantially stable over time. Normally, in particular radioactive isotopes are made by different producers and frequently so in research institutions. Here, the chemical and radiochemical unit must meet strict requirements for medical applications; and legal regulations demand that production take place in environments meeting cGMP standards or employing comparable methods; and the manufacturing quality must be controlled and documented.

Isotopes with half-lifes in a range of a few days or weeks are supplied directly in vessels, while isotopes having shorter half-lifes can be obtained only physico-chemically in situ by means of an accelerator, reactor, or generators containing a radioactive mother isotope and the decayed desired daughter isotopes.

The quantities of radioactive isotopes obtainable with the generator system, as a rule, are limited because of the radioactive decay, the resulting radiation dose and the ensuing balancing of mother and daughter isotopes. Precise planning of treatments is necessary in order to achieve optimum utilization of the radiation dose available since the substances in question are variable as time passes and other substances, likewise of variable nature over time, are used as well in the preparation of medicines.

The biological and chemical basic materials which essentially are stable as time passes and which likewise may be needed for preparing a medicine, as a rule, are prepared according to conventional drug technology. The half-lifes of these basic materials in respect of quality and sterility clearly are superior to those of isotopes and other chemically or biologically unstable substances used. Therefore, no problem arises when keeping them in stock or ordering them in time.

Combining starting materials required for the preparation of a medicine as well as binding or incorporating isotopes or other temporally unstable substances in the medicine, as a rule, are effected by biochemical or physical processes undertaken in a laboratory of a hospital. The biochemical processes for preparing the medicine, as a rule, are carried out manually by hospital staff. That requires a high degree of concentration, practice, speed, and thus training on the whole in order to achieve the highest possible yield of a radioactive isotope or another temporally unstable substance with the requisite quality and safety.

Conventional practice, at present, involves great losses of temporally unstable substances due to a lack of coordination in time and also because of the short lifetime of these substances. Moreover, the purely manual acquisition of data leads to inadequate consideration thereof in quality monitoring. Furthermore, the currently prevailing practice of manually handling radioactive or toxic substances means that the staff suffers from high radiation and toxic exposures and, therefore, is subject to safety risks.

Preparation of a medicine absolutely must be followed by control of the quality to make sure, for instance, that a harmless limit value for radioactive isotopes was not reached and that no toxic or phlogogenic agents are present in it. Moreover, the exact dose to be administered to the patient must be determined.

At present, various possibilities exist for converting a medicine into a form suitable for administration directly before administering it, such as filling it into a container from which syringes then can be filled, directly filling it into syringes for use by a physician, direct aapplication by means of a catheter or needle, and direct production of vessels, like tablets or capsules to be swallowed. In many cases the medicine is filled into a glass container which is emptied through a septum. In accordance with current practice, such steps also are performed manually.

The known process steps described above for making and using a medicine which contains one or more short-lived substances have a number of disadvantages which will be summarized below.

Up to now the data generated during a patient's diagnosis, embracing all the requisite diagnostic and therapeutic measures, including the type and scope of treatment with all the medicines needed, the radiation dose, and the kind of administration have been collected only manually and recorded in patient files. There is no connection or feedback between the diagnosis and the production of the medicine or, if there is, it exists only within the framework of individually drawn up systems made to fit individual clinics.

Expenses for therapy planning and capacity planning run high due to the manually acquired data ending up in often faulty data banks. And yet all the data gathered during patient diagnostics bear unexplored potential for contributing to production planning, logistics planning, control of the manufacturing process as regards the required quantity, concentration, and quality, as well as for therapy planning in consideration of the restrictive conditions existing in a clinical environment. A simple alteration of a therapy plan during the preparatory phase, for example, so as to allow for a change in a patient's constitution is very difficult to be accomplished with present methods.

As regards the preparation and supply of short-lived ingredients of a medicine deficits exist due to a lack in communication between producers and hospitals regarding the intended purpose and the necesssary quality standards of the products to be supplied. The producer, as a rule, has no profound knowledge of the requirements to be met for individual therapies.

Quality data acquired make their way only incompletely into the production of the medicine. As a rule, the person dealing with the preparation in the hospital laboratory has sole responsibility to see those data are properly allowed for.

A link is missing in the logistics chain embracing the necessary quantity and quality as well as automatic reordering and, in general, it is not standardized to cover wide areas and, therefore, too sluggish on the whole. Ordering times of several weeks thus are the rule for the substances needed.

As a consequence of the manual data acquisition the medicines prepared, as a rule, are subjected to quality control only to a limited extent, and the quality control turns out to be very difficult because of the short half-life of the medicines.

Radiation exposure is rather high during administration of the medicines in spite of the use of protective shields. And, on the other hand, the admissible overall radiation exposure of staff members limits the number of individual doses that can be prepared and administered within a certain time interval. At present, the staff is responsible for administering the correct dose. Extensive, error-free quality assurance is not warranted.

It is, therefore, the object of the instant invention to provide a system as well as components thereof and a corresponding method of providing a diagnostic or therapeutic substance combination by which the disadvantages of the state of the art can be diminished and overcome, respectively, and improved production in terms of cost, quality assurance, and documentation of substance combinations and medicines, respectively, especially those containing substances which are temporally unstable can be achieved.

This object is met by a therapy module as claimed in claim 1, a basic module as claimed in claim 6, a system as claimed in claim 13, and a method as claimed in claim 18.

In accordance with the invention, a therapy module is presented for providing a diagnostic or therapeutic substance combination, including at least two interconnectable containers for taking up at least one substance, and means or part of a means for supplying a quantity of the least one substance from one of the containers into another container of the therapy module.

The therapy module according to the invention is suitable for storing, delivering, and providing one or more substances which preferably are substantially invariable as time passes, and further incorporates a container in which, directly before administration to a patient, and especially in a hospital, substances may be brought together and united, respectiovely, with one or more substances, especially also temporally unstable ones which may be supplied from outside, if desired. It is conceivable to design the therapy module at least in part for renewed use or as a disposable item. It is the function of the means for supplying substances from one of the containers to another container of the therapy module to transport the substances between the containers but, at the same time, it may also be used for dosing the substances and for controlling the quantity of an additional substance supplied from outside, if desired.

The chemical/physical structure of the therapy module, including reservoirs, pumps, further components or parts thereof either may be built as a block by suitable manufacturing methods or assembled from standard component parts. Moreover, suitable coatings may be used on the insides of the components employed so as to influence the dosing, quality assurance, and any reaction that possibly may be taking place.

The therapy module according to the invention thus presents a means for locally preparing a diagnostic or therapeutic substance combination directly for administration to a patient. The therapy module can be manufactured inexpensively for use with a great number of substance combinations and it can be delivered either empty or partly or totally filled. Since substances which are temporally variable or instable physically, chemically or biologically, or radioactive substances may be added just before administration substantially automatic manufacture of the therapy module can be achieved, while being controlled as to the condition of the temporally variable substance and the radiation dose, respectively, and contamination of people, like hospital or laboratory staff is largely avoided.

The substance combinations prepared or administered, respectively, can fulfill all the drug and health related requirements in respect of safety for the patient, stability, and biological or chemical half-life, respectively, in particular so if they contain temporally unstable starting substances.

According to an embodiment, the therapy module comprises a plurality of containers of which at least one is connected directly to at least two other containers of the therapy module. Furthermore, at least one of the containers may comprise at least one access, especially for a sensor means, especially for carrying out measures of quality assurance, or a mechanical interface toward the outside of the therapy module. It is preferred by all manufacturers of basic substances and therapy modules to use a substantially standardized form with which certain parameters, such as dimensions and places of access to the therapy module are maintained by everyone, while other features of the structure, like the number of containers in the therapy module and their arrangement as well as the number and kind of technical components provided inside the therapy module may be varied.

According to another embodiment, the therapy module may include one or more pumping means associated with at least one container, dosing means as a means for supplying a quantity of the at least one substance from one of the containers into another container of the therapy module, and/or sensor means or parts thereof. If only parts of the dosing means, sensor means, and/or of a pumping means are provided in the therapy module, while other essential parts of these means are outside and in reusable form for a plurality of therapy modules, the manufacturing cost of the therapy module can be reduced, less building space is needed for the therapy module, and there is only less likelihood of failure of the individual therapy modules.

According to another embodiment, the therapy module includes a housing in which the containers are received, and conduits by which the containers can be interconnected. In this manner contamination of people handling the modules and the substances contained in them can be avoided. Yet it is also conceivable to have some or all the containers connected directly to one another i.e. without additional lines.

According to yet another embodiment, the therapy module is externally controllable and comprises means for receipt of control signals or current supply signals for the means to supply a quantity of the at least one substance from one of the containers into another container of the therapy module and/or for a sensor means. This permits expensive control means and the power supply to be provided externally and be available for multiple use.

According to the instant invention, furthermore, a basic module is provided for providing a diagnostic or therapeutic substance combination, including a receptacle for a therapy module and means for control of one or more means provided on the therapy module to supply a quantity of a substance from one of the containers into another container of the therapy module and/or one or more sensor means, especially for carrying out measures of quality assurance.

The basic module, in the first place, serves for preferably automatic control of preparing a substance combination in a therapy module. In principle, it may be reused any desired number of times and coupled to any number of therapy modules, if desired, provided with one or more basic substances and, if desired, delivered by different drug producers and suppliers. Use of the basic module according to the invention in connection with one or more therapy modules permits substance combinations to be made almost fully automatically, without contact, but with controlled parameters. And it is possible to add in controlled fashion especially temporally unstable substances at the place of the basic module, which place preferably is chosen to be near the place of administration, and to do so directly when preparing the substance combination and prior to administering the medicine.

According to another embodiment, the basic module may include means for detecting at least one of the group of parameters including the kind, quantity, temperature, radiation dose, radiation spectrum, residual lifetime, especially of a short-lived substance, the residence time, concentration, and pH of at least one substance contained in the therapy module. In this manner, the preparation can be controlled and the quality assured of the substance combination and the medicine, respectively, made in the therapy module. Other modules, too, may be equipped additionally or alternatively with such means.

According to another embodiment, the basic module comprises a data processing unit for process control and a data memory means. That permits data management and storing of data acquired by the basic module, especially in respect of the parameters of the substances used for preparing the medicine and the substance combination, respectively, at the time of preparation thereof as well as externally supplied data, such as patient data, and the overall therapy and capacity planning, in the basic module. The basic module also may be furnished with external "quality data" from central data bases so as to stay in keeping with quality requirements for the substance combinations to be prepared.

According to another embodiment it may be provided that the basic module comprises means for controlling the supply of a substance from outside into the therapy module, such as one or more pumping or dosing means. Moreover, the basic module may comprise means for control of one or more accesses or interfaces of the therapy module. In this manner, substances not yet contained in the therapy module but needed for preparation of a substance combination, and especially temporally unstable substances may be added in controlled quantity and controlled condition at the location of the basic module.

According to another advantageous embodiment, the basic module includes at least part of at least one pumping means, dosing means, sensor means and/or evaluation electronics of the sensor means. Dividing the driving, controlling, and energy supplying units between the therapy module and the basic module, e.g. providing a pump head in the therapy module and a pump motor in the basic module, a piezo pump in the therapy module and the corresponding electronics in the basic module, a sensor head in the therapy module and corresponding evaluation electronics in the basic module permits cost reduction of the therapy module, preferably produced as a disposable item or partially for renewed use. The therapy module can be manufactured with smaller building space, and less likelihood of failing of the therapy module can be effected. In this context, it is especially aimed at positioning the largest possible proportion of technical components in the reusable basic module. However, it is a condition for such a distribution of component parts that therapy modules are used which are standardized and uniform, respectively, to a certain degree so that all therapy modules which may be delivered by different manufacturers, if desired, can be used with one basic module. For instance, it is conceivable to locate the accesses to and the connections, respectively, for technical components at the same place in all therapy modules so that parts of those components included in the basic module are compatible with the therapy modules. On the other hand, however, it is not necessary for the therapy modules to contain the same components and the same number of containers.

According to another embodiment, the basic module is adapted to be coupled to a computer means or computer network. Quality data, patient and therapy data, and data for process planning can be communicated via a corresponding network connection, and remote maintenance can be executed. Quality, manufacturing, identification, and monitoring data gathered by the basic module and/or the therapy module likewise may be communicated through this network connection or offered for external use via suitable data carriers, such as a memory card or a writeable RFID chip.

The basic module, furthermore, may serve for energy supply and/or control of electrical components housed in the therapy module and/or other modules and, if desired, it also includes an operator interface, such as a keyboard and/or touch screen by way of which data may be entered and displayed. Apart from a possibility of docking on, such as a mechanical interface for the therapy module, the basic module may comprise further interfaces for other modules.

Another important aspect of the basic unit according to the invention is that, preferably, it is so designed that it will not be contaminated at any time by substances and that the chemical/physical processes will occur exclusively in the therapy module and/or other modules. Contamination of the basic module by substances can be avoided, on the one hand, by directly connecting one or more modules containing at least one substance to the therapy module. Yet it is also conceivable to couple one or more modules containing at least one substance to the basic module. These modules, however, are designed so that a direct connection is possible among one another and with the therapy module, respectively. Hereby substances can be transported between these modules without contaminating the basic module. The interface between the modules and the basic module, for instance, may be used for energy supply of the modules or for establishing control connections to control the connected modules through the basic module.

The invention, furthermore, provides a system, including a therapy module and a basic unit. The system may further include an active ingredient module and an isotope module, respectively, for storing and/or preparing physically, biologically, or chemically short-lived substances, such as radioactive isotopes.

The modular construction of the system according to the invention has various advantages. The substance combination is prepared at the location where the basic module is, i.e. preferably in a hospital and preferably under quality monitoring by the basic module. In this manner, the medicines a patient is to be given can be prepared immediately before administering them and suitable for the patient. Even short-lived substances may be added efficiently and without the need of allowing for decay processes which already happened. Preparing the medicine takes place without any contact between substances and persons, namely substantially automatically, as controlled by the basic module. Depending on the individual therapy planning and the substances contained in or added from outside to the therapy module, completely different substance combinations can be produced under quality and quantity control. The system permits comprehensive monitoring and, if desired, controlling of the processes of preparation and/or therapy, including quality monitoring and feedback to the suppliers of modules and substances.

The system according to the invention permits efficient and flexible handling of a great number of temporally variable substances and especially of radioactive isotopes for a great number of pharmaceutical applications, and it prevents bottlenecks in the supply or provision of temporally variable substances and especially of isotopes while, at the same time, quality monitoring during preparation and safety aspects during preparation and administration of substance combinations can be improved.

Due to the modular design, the reusable technical means which are precious and expensive, respectively, such as quality assurance means, means for dosing substances, means for determining parameters of the substances, driving means, power supply means and/or computer, processor, and data memorizing means may be arranged, at least partly, in the reusable basic module. On the other hand, the therapy module serving for storing in particular substances which essentially are temporally invariable, i.e. suitable to be kept in stock, and for preparing individual substance combinations may be produced as a disposable item or at least partially recyclable. The basic module, furthermore, may be used for therapy data management, such as patient data and the course of treatment, and quality data manufacturing, identification, and monitoring data.

An interface of the basic unit may be occupied for a longer period of time by the active ingredient module which serves for the preparation and keeping, respectively, of short-lived i.e. biologically or chemically unstable substances as well as radioactive substances and which may be filled at times by a manufacturer so that, at the hospital, the active ingredient module merely needs to be coupled to the apparatus. The active ingredient module likewise may be made to be exchangeable and recyclable, respectively. And preferably again part of the technical components, for example, for removal of substances from the active ingredient module or for measuring parameters of the substances contained therein, may be provided in the basic module.

According to another preferred embodiment the system includes a transfer module for keeping and transporting one or more substances or substance combinations. The transfer module may include means for dosing a quantity of the substance or substance combination in response to the proportions of substances already decaying of the one substance or substance combination.

The transfer module, among others, serves for transporting the substance combination made from the therapy module to the patient, and it may be adapted to a certain form of application, for example the shape of a syringe, a catheter or a needle.

Preferably, the transfer module comprises means for performing patient authentification to make sure a patient is correctly assigned and confusion excluded.

According to another embodiment, the therapy module, the active ingredient module, the basic module, and/or the transfer module are interconnectable by way of mechanical, especially sterile interfaces. Moreover, the system may include means for transporting substances from the active ingredient module into the therapy module and/or from the therapy module into the transfer module without contaminating the basic module. Moreover, some or all of the interfaces may designed to be interconnectable and severable without leaks or dead volumes. A simple way of realizing that resides in the provision of a septum (rubber disc) to be pierced by a needle. An alternative, but more expensive solution is a self-locking coupling. Confusion when connecting modules may be precluded by suitable solutions of identification by means of which a module is unambiguously identifiable. That can be done by means of a bar code, by means of radio technology using an RFID chip, or by tactile contact through integrated memory elements or by shape identification, and the like.

The above mentioned modules devised to receive one or more substances, i.e. the therapy module, the transfer module, and/or the active ingredient module may be designed for direct interconnection or also for coupling to the basic module. In the latter case, some or all modules suited to receive one or more substances preferably are so designed that, for conveying substances, they are connectable directly to another such module without contaminating the basic module to which they can be connected. To that end, the modules, for example, may have a finger-like or tube-like portion. The basic module, on the other hand, preferably is formed with a duct at the interfaces provided for connection to those modules and, if desired, may serve for power supply and/or control of the modules connected to the same.

According to another embodiment the therapy module, the active ingredient module, the basic module, and/or the transfer module may comprise shielding against radioactive radiation and/or have a structure preventing the escape of substances. In this manner contamination of hospital staff can be avoided and the number of individual doses as well as the number of patients receiving treatment can be increased.

The active ingredient module preferably is manufactured in standardized form so as to be suitable for use by a plurality of drug and isotope producers, respectively, and suppliers. The supply of active ingredients thus can be standardized, covering a great area without geographical limitation.

According to the invention, moreover, a method is presented for providing a diagnostic or therapeutic substance combination. It includes the steps of providing a therapy module comprising at least a first container and a second container which is adapted to be connected to the first one, and at least one substance held in the first container; arranging the therapy module on a basic module; supplying a quantity of the at least one substance from the first container into the second container of the therapy module under control by the basic module; and supplying a quantity of another substance into the second container.

In accordance with the system according to the invention the method according to the invention likewise has the advantages that the preparation of a substance combination under control by a central processing unit is automatic in the widest sense and takes place under control of the parameters of the substances used.

According to another embodiment, the method may include supplying the other substance from a third container included in the therapy module and adapted to be connected to the second container. The therapy module, for example, may contain a plurality of substances which can be stored without problems and are not subject to short-term changes.

According to another method step, however, another substance also may be supplied from outside to the therapy module. That is advantageous especially with short-lived, chemically and/or biologically unstable substances or radioactive substances since these can be supplied just before administering the medicine, without having to take into account previous variations of the substances and decays, in view of the fact that the condition of the short-lived substance can be determined directly upon supply of the substance combination. Moreover, the requisite quality assurance can be performed directly at the point in time of preparing the medicine in situ at the hospital.

According to another embodiment, the method may include bringing together a plurality of different substances, held in a plurality of containers of the therapy module, in one container of the therapy module that is directly connected to the plurality of containers.

According to yet another embodiment, the method may include the step of supplying to the therapy module a substance which changes over time as regards at least one of its properties, and detecting at least one of the group of parameters including the kind, quantity, temperature, radiation dose, radiation spectrum, residual lifetime, residence time, concentration, and pH of the substance introduced into the transfer module. As part of a quality assurance measure, according to this embodiment, parameters of the substances contained in the substance combination may be determined before or after combining them. These data preferably are stored in a data memory unit which preferably is included in the basic module and may be taken into consideration in automated process control.

In accordance with yet another embodiment according to the invention, the method includes the step of introducing a short-lived, especially a chemically or biologically unstable or a radioactive substance into the therapy module.

The method, furthermore, may include the step of introducing a substance from the therapy module into a transfer module. The transfer module serves for transporting a substance combination prepared to a patient, and it may include means for dosing the proper quantity in dependence on decaying substances contained in the substance combination. Moreover, it may be adapted to the form of application, such as a syringe, a catheter, a needle. The transfer module also may be provided with a means for identifying a patient to make sure an assignment is correctly made and confusion excluded.

According to another embodiment, the method may include supplying substances from and into the individual modules under control of the basic module. The modular design of the system, with important control tasks being accomplished by the basic module, offers controllability of the process squences and data acquisition so that substantially complete automation is achievable and alterations in process sequences are easy to be made.

According to the invention, moreover, a computer program is provided, including a program code which, once installed in a computer, causes the latter to execute the method according to the invention. Likewise provided is a computer-readable carrier on which the computer program is implemented. Also, a computer may be provided which is equipped to conduct the procedure according to the invention.

The method according to the invention as well as the therapy module, the basic module, and the system may be employed for a great many therapeutic and diagnostic purposes. Especially preferred are applications where it is advantageous to prepare a therapeutic or diagnostic substance combination near the place of administration thereof, such as in a hospital.

Exemplary applications include the administration of substance combinations containing radioactive nuclides (radioisotopes) for cancer treatment and diagnosis, in pain therapy, and for wound dressing, for example. The preferred isotopes used in this context are those having suitable half-lifes and dosage rates, and the smallest possible radius of action.

In diagnostic applications, isotopes permit metabolic processes to be rendered visible and cell species to be localized. To that end, the isotopes are incorporated in molecules which take part in metabolism, or they are coupled to antibodies and similar proteins which in turn are bound to specific receptors. Here, the goals are small dosage rates and a very short half-life of a few hours and a few minutes, respectively, with the aim of keeping the patient's exposure as low as possible.

For diagnostic purposes, moreover, radioactive substances may be used in PET tomography, X-ray or CT-examinations, or also fluorescent substances.

All substance combinations made in accordance with the system and method of the invention must meet drug and health related technical requirements. This means that especially chemically or biologically unstable starting substances when combined with other substances must yield a stable, safe, and logistically manageable substance combination after the preparation procedure.

The modular system according to the invention as well as individual components thereof and the method according to the invention will be described below on the basis of an exemplary embodiment.

The FIGURE is a diagrammatic illustration of an embodiment of the integrated radiopharmaceutical product quality assurance and safety system (IQS) according to the invention.

The system shown in the FIGURE includes a therapy module 1 comprising at least two containers (not shown) adapted to be connected to each other and to hold at least one substance, and one or more means, especially pumping or dosing means for supplying at least one substance from one of the containers into another container of the therapy module 1, or at least parts of these means. The therapy module includes interfaces 7, 9 toward individual containers or modules and may also include one or more accesses (not shown) from outside for supply of substances or introduction of sensor means.

The therapy module 1 may also be provided with a plurality of containers intended to hold basic substances or with at least one additional container connected directly to at least two other containers and being used for preparing a substance combination in the therapy module 1. The internal structure of the therapy module, the number of containers inside it and their connections, the number of pumping means and/or sensor means may vary with different therapy modules. In principle, also the dimensions of the therapy module are variable, even though a size corresponding approximately to a video cassette is preferred. The therapy module preferably has the shape of a parallelepiped having a lateral length of preferably less than 20 cm, especially preferred being less than 5 cm, a width of preferably less than 10 cm, especially preferred being less than 2.5 cm, and a height of preferably less than 5 cm, especially preferred being less than 1 cm.

The therapy module 1 and the chemical/physical structure it houses, respectively, either are produced by suitable manufacturing methods as an individual mono-block including reservoirs and pumps, if desired, or they are made up of standard components. Suitable materials for manufacture of the basic module and especially of the containers and of conduits for connecting them include plastics, metals, especially non-oxidizable metals, and glass or combinations of the same. Furthermore, suitable coatings may be employed on the inside of components used in order to be able to influence the dosing, quality assurance, and ongoing reactions.

The system further comprises a basic module 2 having a receptacle 3 into which the therapy module 1 may be introduced. The basic module 3 includes an operating panel 6 through which parameters may be input for control of processes and by which data that may have been gathered or process sequences can be displayed. Acording to the embodiments shown, the basic module 2 further preferably comprises at least part of drive, power supply, and sensor means, especially for quality assurance, for the therapy module 1, such as one or more pump motors for pump heads provided, if desired, in the therapy module 1, and drive or evaluation electronics for piezo pumps or sensor heads provided, if desired, in the therapy module. If desired, the sensor means also may be provided completely at the basic module 2.

The sensor means may include means for detecting parameters of the substances contained in the therapy module 1 and of substance combinations prepared, for example, the kind, quantity, temperature, radiation dose, radiation spectrum, residual lifetime, residence time, concentration, and pH. Characteristics of quality and condition, respectively, of the substances and substance combinations, respectively, thus can be detected and quality assurance of the substance combination can be effected.

Contactless sensor means are preferred for use, e.g. detectors for radiation measurement, means for measuring light refraction, among others, to determine the presence and type of a liquid, light barriers for determining the presence of solids, means for measuring changes in color, especially for detecting and picking up the course of chemical reactions.

Other sensors include gamma sensors, beta sensors, drill hole scintillation counters, HPLC columns, CCDs and video cameras, etc.

The provision of these multiple use components in the basic module 2 rather than the therapy module 1 permits production costs of the therapy module 1 to be lowered, the therapy module 1 to be manufactured with smaller dimensions, and it lowers the probability of failure of the therapy module 1. The basic module 2 can be used with a plurality of therapy modules 1 which may differ in structure.

Due to its modular structure, the basic module 2 at no time gets into contact with the substances or substance combinations, and the ongoing processes take place exclusively in the therapy module 1, relying on other modules, if desired. Persons involved in the preparation and administration of the substance combination likewise do not get into contact with the substances.

The basic module 2 preferably further incorporates an information system which preferably includes a processor for storing data, linking data, for instance, for therapy and capacity planning and/or for indicating the technical condition of individual modules. Furthermore, the basic module 2 preferably offers access 8 to a local or global network, such as the internet so that data from other participating components, such as the drug producers, may be incorporated in the process control and data acquired by the basic module 2 may be sent to drug producers or other users.

The basic module 2 shown in the FIGURE is merely exemplary and could also have an altered structure and a different form, respectively. In particular the receptacle 3 for the therapy module 1 could be designed such that therapy modules 1 of different dimensions or several therapy modules 1 at the same time could be connected.

As may be gathered from the FIGURE the system also includes an active ingredient module 4 which preferably may be coupled by way of another interface or directly to the therapy module 1. In the case of the embodiment illustrated, the active ingredient module 4 is designed for coupling to the basic module 2. To protect the basic module 2 from contamination by substances, the active ingredient module 4 comprises a finger-like portion (not shown) at the side intended for connection to the basic module 2. The finger-like portion is insertable into an opening or through hole (not shown) in the basic module 2 leading to the therapy module 2 and directly connectable to the therapy module 2 so that substances are transferable without getting into contact with the basic module 2.

The active ingredient module 4 serves for storing and preparing, respectively, chemically or physically unstable or radioactive substances. The active ingredient module 4 preferably is secured against leaks of toxic substances or equipped with radiation shielding. The short-lived substances withdrawn from the active ingredient module 4 are introduced directly and as controlled by the basic module 2 into a container of the therapy module 1 serving for preparation of the substance combination. Since the use of the basic module 2 and the location thereof, respectively, preferably are in a hospital the short-lived substances may be used for preparation essentially without delay in time shortly before the substance combination is administered to a patient. Exemplary temporally unstable substances include radioactive isotopes, such as the sources of beta radiation: yttrium, iodine, holmium, fluorine, rhenium, lutetium; and of alpha radiation, and also other chemically or biologically unstable substances which may be used, for example, in chemotherapy. According to an embodiment half-lives of chemically or biologically unstable or radioactive substances employed therapeutically or diagnostically are less than two weeks, preferably less than 100 hours, especially preferred being less than 50 minutes.

A transfer module 5 can be connected to the basic module 2 through another interface 7. To protect the basic module 2 from contamination by substances, the transfer module 5, too, comprises a finger-like portion (not shown) at the side destined for connection to the basic module 2. The finger-like portion is insertable into an opening (not shown) provided in the basic module 2 and connected to the interface for the therapy module 2. Thus the transfer module 5 is connected directly to the therapy module 1, and substances are exchangeable between the modules without contaminating the basic module 2. For example, the quality control of substances or substance combinations transferred into the transfer module 5 may take place in that portion of the transfer module which is passed through the basic module 2.

The transfer module 5 serves to take up a substance combination prepared in the therapy module 1 and to transport it so as to be administered to a patient. Preferably the transfer module 5 is adapted to a certain form of application, such as a syringe, catheter, or needle and comprises a corresponding connector interface 10. Moreover, it may include means for dosing the correct quantity, if desired, in response to the substances it contains which have decayed since filling. Depending on the form of application, it may include a shield against toxic and/or radioactive substances for persons getting in touch with it, like hospital staff or physicians. Moreover, the transfer module 5 may incorporate means (not shown) for identification and association with a specific patient so that the substances it contains will be released only upon unambiguous identification and assurance that the temporal quality parameters are met. Furthermore, it may include an information interface 9 and a corresponding data storing means to take over data, such as patient data, identification data, therapy and diagnosis data, product and quality data.

The transfer module 5, too, is merely exemplary and may also be of different design. In particular, it is conceivable to provide functions and features, respectively, of the transfer module 5 in the therapy module 1 so that the transfer module 5 may be dispensed with, if desired.

Further modules (not shown) adapted for connection to the basic module 2 may be provided and designed in such a way that they can be connected to the therapy module 1 or the tranfer module 5 in the manner described above. Alternatively, it is conceivable to devise some or all modules for direct coupling to the therapy module 1.

The course of an exemplary therapeutic process with the support of the system according to the invention and the method, respectively, will be described below.

To begin with, a physician examining a patient determines the necessary diagnose or therapy. The resulting data are entered into the ICS information system and, if desired, via the detour of the information system, into a hospital.

Subsequently, a therapy or diagnosis plan is drawn up, preferably in the basic module 2 of the IQS system, based on the quantity available of a radioactive isotope and a chemically unstable substance, respectively, with the assistance of staff especially trained for that purpose, if desired. If desired, not only the aspects relating to the medicine and the patient, such as kind, quantity, times of administration etc. of the medicine but also apparatus, laboratory capacity, availability of staff, and treatment capacities of the hospital are considered in the therapy plan. The therapy plan may be adapted and adopted by a responsible person, such as the head of the laboratory of nuclear medicine or the head of the oncology department.

On the basis of the therapy plan, orders for one or more therapy modules needed are released preferably automatically.

During this preparatory period, changes in the state of health of the patient can be considered continuously in the therapy/diagnosis planning.

On the therapy day, the requisite quantity of a temporally unstable substance or, e.g. the isotope for this day, is provided automatically in the active ingredient module and booked for the individual treatments. For this purpose the active ingredient module is connected to the IQS basic module 2.

At the planned time of treatment, the therapy module 1 is inserted in the basic module 2, the respective patient data are fetched, and the corresponding transfer module 5, for example, a syringe applicator is connected. With the assistance of the basic module 2 of the IQS system the modules connected are identified, their identity and the stored quality data are checked, the desired quantity for the therapy/diagnosis is determined or fetched, alarm messages are issued in the event of errors, or the preparation procedure is initiated. All the data generated at this time are memorized and added to the patient data and production data in the basic module 2.

During the preparation procedure, the quantity needed of an isotope solution is pumped from the active ingredient module 4 into the therapy module 1. There, it is mixed, for instance, with labeled monoclonal antibodies (MAB) already present in the therapy module 1. The procedure is optimized by adding radical binders, such as vitamin C, buffer solution, and the like, and correct chemical values are set. Furthermore, it is made sure in the therapy module 1 that suitable environmental conditions, such as a predetermined pressure and a predetermined temperature are assured to achieve the best possible procedure. Unbound isotopes, for example, are separated from the substance combination in a size exclusion column which likewise may be integrated in the therapy module 1 or provided at the basic module 2, and the quality of the product can be measured by means of a chromatography step in that the ratio is measured between bound and unbound isotopes. All the data acquired are memorized via the IQS basic module 2.

Finally, the product and the substance combination, respectively, are transferred into the transfer module 5. Upon administration of the substance combination(s) the used therapy module 1 is automatically sent to recycling, if desired, by the IQS basic module 2.

The transfer module 5 is separated from the IQS basic module 2 and transported to the patient. Administration of the substance combination it contains may be effected by introducing the substance combination which is bound to antibodies into the body, i.e. into the blood circuit or into body cavities resulting from surgery, by injecting it into natural joints or artificial orifices in the body made by surgical interventions for irritating or destroying tissue, by inserting a catheter into a blood vessel for locally influencing tissue, by binding a substance combination to peptides (proteins), sugar, or other substances to be included in the metabolism for imaging processes or cancer therapy.

Based on the time elapsed and measured internal data, the change i.e. the decay of the product can be checked, if desired, with the aid of the transfer module 5, and it can be made sure that a defined decay time is not exceeded because the transfer to the patient lasted too long. Likewise, with the aid of the transfer module 5, a patient can be identified by means of biometric data, a card, or a bar code, etc., and the amount to be applied of the substance combination contained in the transfer module 5 can be determined. Also the administration itself which may be undertaken, for example, by intravenous injection can be controlled by the transfer module by means of a blocking device it includes and a suitable interface, respectively. The relevant parameters in this context are the quantity, the prevailing pressure, and the injection rate. The special automatic transfer module 5 relieves the physician of the time-consuming slow injection.

Subsequently, the transfer module 5 is sent to recycling and, if desired, the isotope module is sent to a supplier for refilling.

Finally, the patient data reflecting the successful treatment and, if desired, the radiation dose applied are memorized in the IQS basic module 2 or transmitted to a patient file kept at another place, whereby procedures can be improved continuously or new study data collected.

The features indicated in the instant specification, drawing, and claims may be significant to the invention, both individually and in any desired combination.

The invention claimed is:

1. A structurally separate therapy module for providing a diagnostic or therapeutic substance combination, comprising:

a housing:

at least two containers received in the housing, interconnected by at least one conduit, and each for taking up at least one substance;

at least one of said at least two containers being connected to at least one access arraged in said housing, said access being externall controllable for a supply of the at least one substance from outside to said at least one of said at least two containers; and further comprising only part of at least one externally controllable pump means for supplying a quantity of the said at least one substance from one of said at least two containers into the other of said at least two containers of the therapy module.

2. The therapy module according to claim 1, wherein the at least two containers comprises at least three containers, wherein at least one of the at least three containers is connected directly to two other of the at least three containers of the therapy module.

3. The therapy module according to claim 1, wherein at least one of the at least two containers comprises at least one access for a sensor.

4. The therapy module according to claim 1, further comprising at least one of one or more pump means, dosing means, and sensor means, or parts thereor, associated with at least one of the at least two containers.

5. The therapy module according claim 1, wherein the therapy module is externally controllable, further comprising means for receipt of control signals or current supply signals for a means for supplying a quantity of the at least one substance from one of the at least two containers into another container of the therapy module or for a sensor means or a combination of the means for supplying a quantity of the at least one substance and the sensor means.

6. A system for providing a diagnostic or therapeutic substance combination, comprising:

a structurally separate therapy module, wherein the therapy module comprises:

a housing:

at least two containers received in the housing, interconnected by at least one conduit, and each for taking up at least one substance;

at least one access arranged in said housing, said access being externally controllable for a supply of the at least one substance from outside to said at least one of said at least two containers;

only part of at least one externally controllable pump means for supplying a quantity of the at least one substance from one of the at least two containers into another of the at least two containers of the therapy module; and a basic module, wherein the basic module comprises a receptacle for the therapy module, and means for controlling a supply of the at least one substance from outside to said at least one of said at least two containers of the therapy module.

7. The system according to claim 6, further comprising an active ingredient module for at least one of storing and preparing short-lived substances.

8. The system according to claim 7, wherein short-lived substances comprise at least one of chemically unstable substances, biologically unstable substances, and unstable radioactive isotopes.

9. The system according to claim 7, further comprising a transfer module for storing and transporting one or more substances or substance combinations, wherein the transfer module comprises means for dosing a quantity of the substance or substance combination in response to the substance proportions already decayed of the one substance or substance combination.

10. The system according to claim 9, wherein at least two of the group comprising the therapy module, the active ingredient module, the basic module, and the transfer module are interconnected by way of at least one interface, the system further comprising at least one of means for transporting substances from the active ingredient module into the therapy module and means for transporting substances from the therapy module into the transfer module.

11. The system according to claim 9, wherein at least one of the therapy module, the active ingredient module, the basic module, and the transfer module comprises at least one of a shield against radioactive radiation and a structure which prevents substances from exiting.

12. A method for providing a diagnostic or therapeutic substance combination, comprising:

providing a structurally separate therapy module, wherein the therapy module comprises:

a housing;

at least two containers received in the housing, interconnected by at least one conduit, and each for taking up at least one substance;

at least one of said at least two containers being connected to at least one access arranged in said housing, said access being externally controllable for a supply of the at least one substance from outside to said at least one of said at least two containers, and further comprising only part of at least one externally controllable pump means for supplying a quantity of the at least one substance from one of said at least two containers into the other of the said at least two containers of the therapy module, wherein the at least two containers comprise at least a first container and a second container adapted to be connected to the first container, and the at least one substance held in the first container;

arranging the therapy module at a basic module, wherein the basic module comprises a receptacle for the therapy module;

supplying a quantity of the at least one substance from the first container into the second container of the therapy module under control by the basic module; and supplying a quantity of another substance into the second container.

13. The method according to claim 12, wherein the another substance is supplied from a third container included in the therapy module and adapted to be connected to the second container.

14. The method according to claim 12, wherein the quantity of another substance is supplied from outside to the therapy module.

15. The method according to claim 12, further comprising bringing together a plurality of different substances, held in a plurality of containers of the therapy module, in one container of the therapy module that is directly connected to the plurality of containers.

16. The method according to claim 12, further comprising:

introducing into the therapy module a substance which changes over time as regards at least one of its properties, and detecting at least one parameter selected from of a group of parameters consisting of kind, quantity, temperature, radiation dose, radiation spectrum, residual lifetime, residence time, concentration, and pH of the substance introduced into the therapy module.

17. The method according to claim 12, further comprising introducing a short-lived substance into the therapy module.

18. The method according to claim 17, wherein the short-lived substance comprises a chemically or biologically unstable or a radioactive substance.

19. The method according to claim 12, further comprising introducing at least one substance from the therapy module into a transfer module.

20. The method according to claim 12, wherein the introduction of the substances is effected under control of the basic module.

21. A therapy module for providing a diagnostic or therapeutic substance combination, comprising: a housing at least two containers received in the housing, interconnected by at least one conduit, and each for taking up at least one substance, wherein the therapy module is adapted to be coupled with a basic module, wherein the therapy module comprises only part of at least one externally controllable pump means for supplying a quantity of the at least one substance from one of said at least two containers into the other of said at least two containers of the therapy module, and a mechanical interface controllable by said basic module, said mechanical interface being adapted for a direct connection of the therapy module with a further module for conveying of a substance between the modules, subject to control by the basic module.

* * * * *

UNITED STATES PATENT AND TRADEMARK OFFICE

CERTIFICATE OF CORRECTION

PATENT NO. : 8,403,906 B2
APPLICATION NO. : 11/793467
DATED : March 26, 2013
INVENTOR(S) : Oliver Buck et al.

It is certified that error appears in the above-identified patent and that said Letters Patent is hereby corrected as shown below:

Title Page, Item (54) and in the Specifications, Column 1, in the Title:
"INTEGRATED PHARMACEUTICAL PRODUCTION, QUALITY, ASSURANCE, AND SAFETY SYSTEM (IQS)" should read --INTEGRATED PHARMACEUTICAL PRODUCTION, QUALITY ASSURANCE, AND SAFETY SYSTEM (IQS)--.

In the Specifications

Column 3,
Line 60, "respectiovely" should read --respectively--.

Column 8,
Lines 11-12, "may designed" should read --may be designed--.

Column 13,
Line 20, "diagnose or" should read --diagnosis or--.

In the Claims

Column 14,
Line 63, "externall" should read --externally--.

Column 14-Column 15,
Line 67-Line 1, "of the said" should read --of the--.

Column 15,
Line 14, "thereor," should read --thereof,--.

Signed and Sealed this
Thirtieth Day of July, 2013

Teresa Stanek Rea
*Acting Director of the United States Patent and Trademark Office*

Column 16,
Line 25, “of the said” should read --of said--.
Line 55, “from of a” should read --from a--.

Column 17,
Line 5, “comprising: a housing” should read
--comprising:
a housing,--.